US007640934B2

(12) United States Patent
Zollinger et al.

(10) Patent No.: US 7,640,934 B2
(45) Date of Patent: Jan. 5, 2010

(54) INFANT NASAL INTERFACE PRONG DEVICE

(75) Inventors: Chris Zollinger, Chino Hills, CA (US); Brian Pierro, Yorba Linda, CA (US)

(73) Assignee: CareFusion 2200, Inc., San Diego, CA (US)

( * ) Notice: Subject to any disclaimer, the term of this patent is extended or adjusted under 35 U.S.C. 154(b) by 285 days.

(21) Appl. No.: 11/292,808

(22) Filed: Dec. 2, 2005

(65) Prior Publication Data
US 2007/0125387 A1   Jun. 7, 2007

(51) Int. Cl.
*A61M 15/08* (2006.01)
(52) U.S. Cl. .......................... 128/207.18; 128/200.24; 128/206.11; 128/203.18; 128/203.22; 128/858; 128/200.26
(58) Field of Classification Search ............ 128/200.24, 128/207.18, 206.11, 203.18, 203.22, 858, 128/200.26
See application file for complete search history.

(56) References Cited
U.S. PATENT DOCUMENTS 4,367,735 A * 1/1983 Dali ....................... 128/207.18
4,782,832 A * 11/1988 Trimble et al. ............ 128/207.18
7,353,826 B2 * 4/2008 Sleeper et al. ............ 128/206.11
2002/0053347 A1 * 5/2002 Ziaee ..................... 128/207.18
2004/0065330 A1   4/2004 Landis
2005/0051177 A1   3/2005 Wood et al.

OTHER PUBLICATIONS

PCT Search Report (9 pgs.).

* cited by examiner

*Primary Examiner*—Patricia Bianco
*Assistant Examiner*—Nihir Patel
(74) *Attorney, Agent, or Firm*—Dicke, Billig & Czaja, PLLC

(57) ABSTRACT

An infant nasal interface prong device for use with an nCPAP system. The device includes first and second nasal prongs and a base. Each prong includes a bellows segment, a tip, and a lumen. The tip extends from the bellows segment to a tip end and is adapted for insertion with an infant's naris. The lumen extends through the tip and the bellows segment. In an undeflected state, a central axis of the lumen along the bellows segment is transversely offset from the lumen axis at the tip end. The base is connected to each of the nasal prongs and is adapted for coupling to a CPAP generator. The bellows segment renders the corresponding prong highly flexible relative to the base. The offset positioning of the tip end promotes desired positioning of the base/CPAP generator, relative to the patient and more closely conforms to the expected nasal anatomy.

28 Claims, 6 Drawing Sheets

INFANT NASAL INTERFACE PRONG DEVICE

BACKGROUND

The present invention relates to patient nasal interface devices for use with continuous positive airway pressure (CPAP) systems. More particularly, it relates to a nasal interface prong device for delivering CPAP therapy to the nasal airways of a patient, such as an infant.

CPAP therapy has been employed for many years to treat patients experiencing respiratory difficulties and/or insufficiencies. More recently, CPAP therapy has been advanced as being useful in assisting patients with under-developed lungs (in particular, infants and especially premature infants or neonates) by preventing lung collapse during exhalation and assisting lung expansion during inhalation.

In general terms, CPAP therapy entails the continuous transmission of positive pressure into the lungs of a spontaneously breathing patient throughout the respiratory cycle. A CPAP system generally includes a CPAP generator adapted to create or generate a continuous positive airway pressure within one or two tubes, along with a patient interface device connected to the generator that serves as a conduit for transfer of inhaled and exhaled gases. The CPAP generator can assume a variety of forms, including a fixed flow, ventilator-type system, or a variable flow system.

Similarly, CPAP can be delivered to the patient using a variety of patient interface devices, for example an endotracheal tube. With infants, however, it is desirable to employ a less invasive patient interface device, in particular one that interfaces directly or indirectly with the nasal airways via the patient's nares. Such systems are commonly referred to nasal continuous positive airway pressure ("nCPAP") systems.

With nCPAP systems, the patient nasal interface device is typically either a mask or a dual prong body. The nasal mask is characterized as defining a single cavity that is placed over the patient's nose. The cavity is fluidly connected to the CPAP generator and thus provides a conduit between the CPAP generator and the patient's nasal airways. While non-invasive, it is sometimes difficult to consistently achieve and maintain a fluid-tight seal between the mask cavity and the nasal airways. This is especially true with infants whom otherwise have smaller facial features and thus facial surface area against which the mask can be applied. Conversely, the dual prong device includes two prongs or cannulas each fluidly connected to the CPAP generator and sized for insertion within a respective naris of the patient. With this technique, a relatively stable fluid seal can readily be accomplished between the prongs and the nasal airways. Unfortunately, however, the inventors have discovered several possible shortcomings with currently available infant CPAP nasal interface prong devices.

For example, nasal interface prong devices are designed to satisfy an overriding goal of achieving and maintaining a fluid seal within the patient's nares. The conventional approach for ensuring a fluid seal is to form the prongs to be somewhat soft, along with having an enlarged diameter along a portion of a length thereof (e.g., a flared tip end or enlarged tip base). This enlarged diameter essentially presses into or lodges against the patient's naris tissue/membrane upon insertion. To this end, though soft, conventional prong configurations have little or no mobility (e.g., cannot axially compress or move laterally), leading to distinct pressure points along the tip end/naris interface. For many patients, especially infants, this interaction can be quite painful, causing the patient to resist insertion of the nasal prongs and/or long-term usage. In fact, the delicate tissue associated with the patient's nares (and especially a premature infant's nares) can be damaged by long-term contact with the nasal prongs, resulting in pressure sores and even necrosis. Unfortunately, simply softening the prong material is not a viable solution, as it may lead to kinking of the prong(s) during use.

Along these same lines, the immobile nature of the conventional nasal interface prong device cannot accommodate any misalignment of the CPAP generator relative to the patient's nose. When the CPAP generator is later moved relative to the patient to correct this misalignment, the nasal interface prong device will also move in a similar fashion, again potentially leading to painful pressure points within the patient's nares. While efforts have been made to incorporate a flexible segment into the nasal prong design, (e.g., Landis, U.S. Publication No. 2004/0065330), other concerns arise, such as kinking of the flexible section or insufficient lateral resistance to prong collapse during insertion within the naris. Further, with other attempts (e.g., Trimble et al., U.S. Pat. No. 4,782,932), human nasal anatomy has not been fully addressed, nor have the anatomical peculiarities commonly encountered with infants been accounted for. For example, the nasal septum is under-developed in many infants, and in particular premature infants. This, in turn, dramatically affects the uniformity of a particular naris diameter. Because available flexible nasal prong designs cannot self-correct for the naris diameter actually encountered, it is necessary to have a relatively large number of differently-sized nasal prong devices on hand. As might be expected, healthcare facilities would greatly prefer to not maintain a large inventory of differently-sized products; similarly, physicians may find it difficult and time consuming to select the optimal nasal prong device from a large number of available sizes through trial-and-error.

In light of the above, a need exists for an improved nasal interface prong device for use with an nCPAP system, especially for infant patient applications.

SUMMARY

Some aspects in accordance with principles of the present invention relate to an infant nasal interface prong device for use with a nasal continuous positive airway pressure (nCPAP) system. The device includes first and second nasal prongs and a base. Each prong includes a bellows segment, a tip, and a lumen. The tip extends from the bellows segment and is adapted for insertion with an infant's naris. Further, the tip terminates in a tip end opposite the bellows segment. The lumen extends through the tip and the bellows segment. In an undeflected state, a central axis of the lumen as defined by the bellows segment is transversely offset from a central axis of the lumen as defined at the tip end. The base is connected to each of the nasal prongs and is adapted for coupling to a CPAP generator. In addition, the base defines first and second passages fluidly connected to respective ones of the lumens. With this configuration, the bellows segment renders the corresponding prong highly flexible such that the respective tips radially pivot relative to the base. Further, the offset positioning of the tip end relative to the bellows segment promotes desired positioning of the base, and thus of a CPAP generator assembled thereto, relative to the patient while at the same time more closely conforming to the expected nasal anatomy. In one embodiment, the tip is curved in longitudinal extension from the bellows segment. In another embodiment, the bellows segment is characterized by a reduced wall thickness as compared to a wall thickness of the tip, and is configured to impart an inward bias onto the tip.

Other aspects in accordance with principles of the present invention relate to an infant nasal continuous positive airway pressure (nCPAP) device for use in an nCPAP system. The device includes an nCPAP generator and an infant nasal interface prong device. The nCPAP generator includes first and second tubes, and is adapted to generate a continuous positive airway pressure within each of the tubes. The infant nasal interface device is mounted to the tubes and includes first and second prongs, and a base. Each of the prongs includes a bellows segment, a tip, and a lumen. The tip extends from the bellows segment and is adapted for insertion within an infant's naris. Further, the tip terminates in a tip end opposite the bellows segment. The lumen extends through the tip and the bellows segment such that in an undeflected state, a central lumen axis along the bellows segment is transversely offset from the central lumen axis at the tip end. The base, in turn, is connected to each of the nasal prongs and is coupled to the CPAP generator. In this regard, the base defines first and second passages each fluidly connected to a respective one of the lumens. Further, the passages are fluidly connected to respective ones of the tubes upon final assembly. In one embodiment, the base of the interface device and a housing of the CPAP generator define corresponding, non-symmetrical shapes.

Yet other aspects in accordance with principles of the present invention relate to an infant nasal interface prong device for use with an nCPAP system. The device includes first and second prongs and a base. Each prong includes a bellows segment, a tip, and a lumen. The tip is adapted for insertion within an infant's naris and has a tip body extending from the bellows segment and terminating at a tip end. Further, the tip body defines a top side forming a convex curve in longitudinal extension and a bottom side forming a concave curve in longitudinal extension. The lumen extends through the prong and is open at the tip end. With this in mind, in an undeflected state of the prong, a central axis of the lumen as defined by the bellows segment is transversely offset from the central axis of the lumen as defined at the tip end. The base is connected to each of the nasal prongs and is adapted for coupling to a CPAP generator. In addition, the base defines first and second passages fluidly connected to respective ones of the lumens. In this regard, the prongs extend in a juxtaposed fashion relative to the base. The bellows segment of each prong is configured to be non-symmetrical relative to an axis of the corresponding tip.

DETAILED DESCRIPTION

Figure 1:
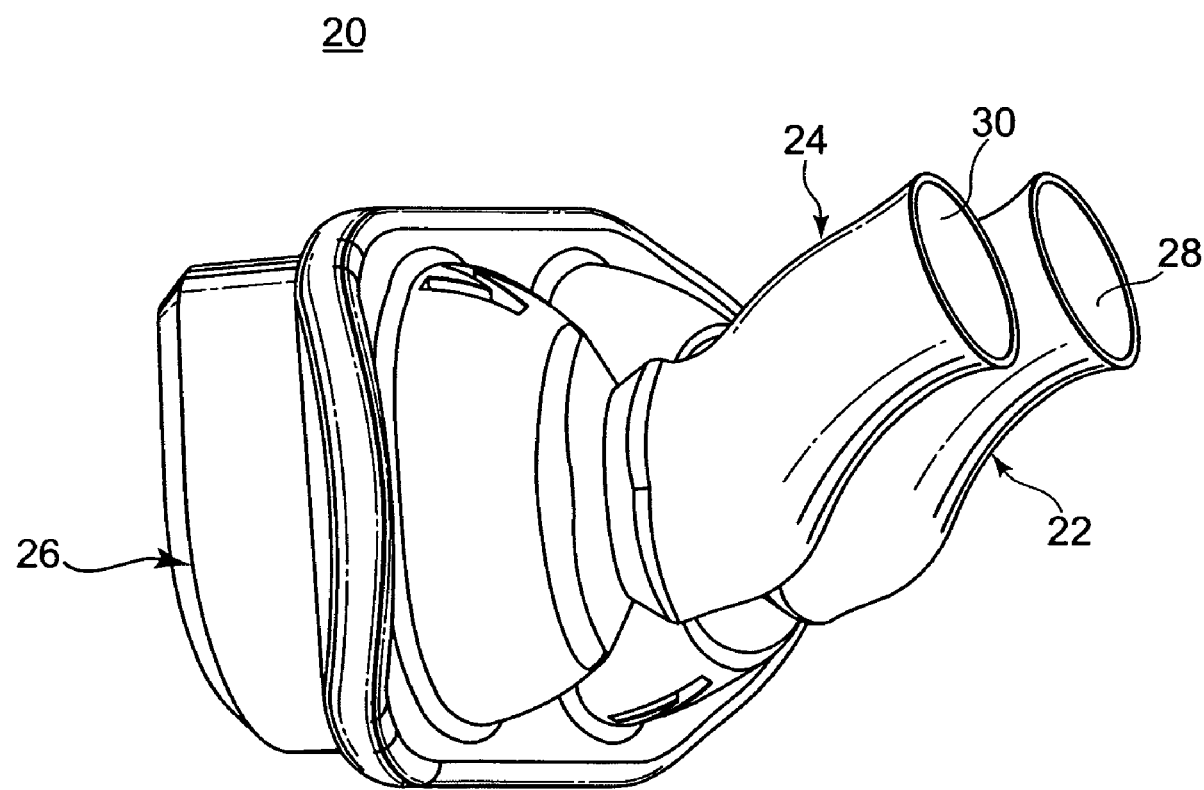
FIG. 1 is a front perspective view of an infant nasal interface prong device in accordance with principles of the present invention.

One embodiment of an infant nasal interface prong device 20 for use with a nasal continuous positive airway pressure (nCPAP) system is shown in FIG. 1. The interface device 20 includes a first prong 22, a second prong 24, and a base 26. Details on the various components are provided below. In general terms, however, the prongs 22, 24 extend in a generally juxtaposed fashion from the base 26, and each define a lumen 28, 30 (referenced generally), respectively. The base 26 is configured to establish a fluid connection between an nCPAP generator (shown at 150 in FIG. 5A) and the lumens 28, 30. To this end, the first and second prongs 22, 24 are each configured for insertion within a patient's naris. Further, the prongs 22, 24 are adapted to be highly flexible, allowing for longitudinal movement and lateral/transverse pivoting relative to the base 26 without collapsing of the corresponding lumen 28, 30. As such, the patient interface device 20 readily accommodates any slight misalignments upon securement to the patient, whereby a tip portion of each of the prongs 22, 24 effectively"floats" relative to the base 26. As described below, in some embodiments, the interface device 20 incorporates additional features that further reduce possible patient discomfort.

As used throughout the specification, relative directional terminology, such as"proximal" and"distal" are used with reference to a position of the interface device 20 relative to a patient to whom the interface device 20 is applied. Thus, "proximal" is closer to the patient as compared"distal". Further, spatial terminology, such as "horizontal," "vertical," "top," "bottom," etc., are with reference to an upright orientation of the device 20 as shown in FIG. 1, but are in no way limiting.

The interface device 20 is preferably an integral, homogenous structure, formed of a surgically safe, compliant material capable of achieving a fluid seal when applied to a patient's skin and nares. For example, and in one embodiment, the interface device 20 is a molded silicone part. Alternatively, other materials such as soft vinyls, thermoplastic elastomers, etc., are also acceptable. However, reference to certain dimensional attributes in the following discussion relates to one embodiment in which the interface device 20, and in particular each of the prongs 22, 24, is a homogenous, thin-walled structure formed of silicone or silicone-like material.

Figure 2A:
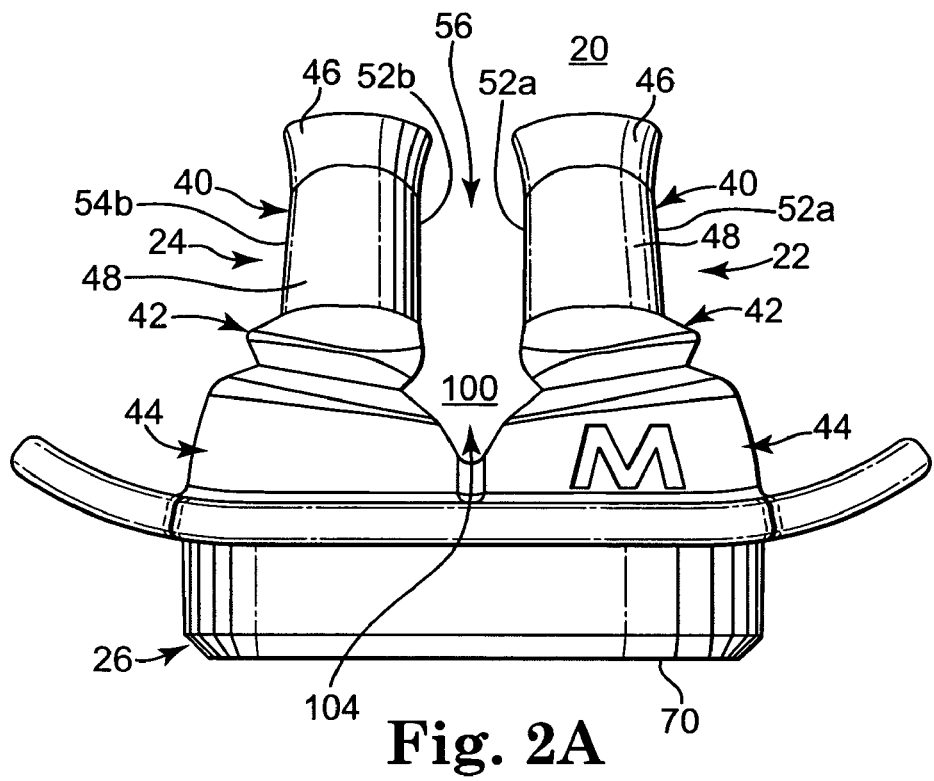
FIG. 2A is a bottom plan view of the interface device of FIG. 1.
Figure 2B:
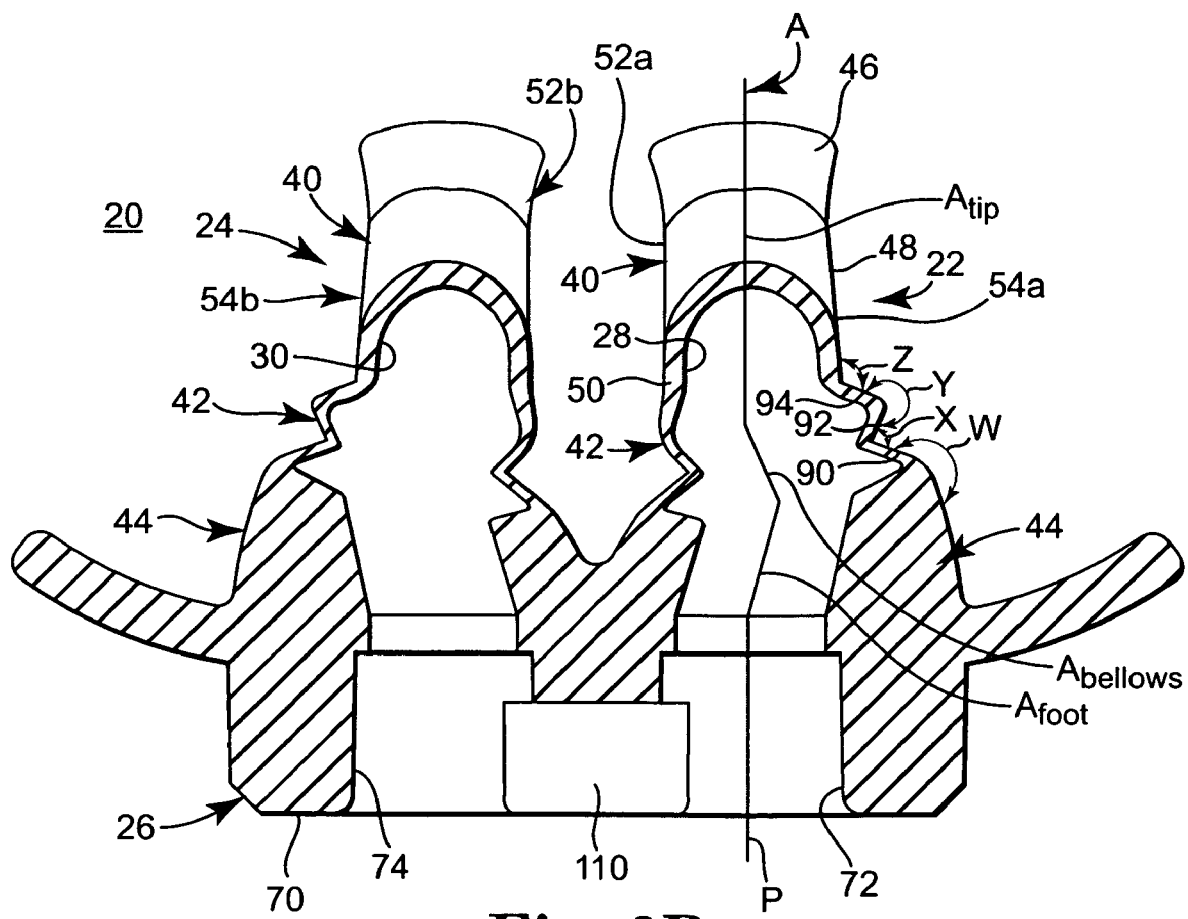
FIG. 2B is a bottom, longitudinal cross-sectional view of the interface device of FIG. 1.

With the above general parameters in mind and with specific reference to FIGS. 2A and 2B, in one embodiment each of the prongs 22, 24 is defined by or includes a tip 40, a bellows segment 42, and a foot 44. The prongs 22, 24 extend in a generally juxtaposed fashion from the base 26, and are identical. Thus, the following description of the first prong 22 applies equally to the second prong 24.

The lumen 28 extends through the tip 40, the bellows segment 42, and the foot 44, such that the prong 22 is a generally tubular body defining a lumen central axis A (referenced generally in FIG. 2B). A spatial orientation of the lumen central axis A varies between the tip 40, the bellows segment 42, and the foot 44, with these variations being reflected in the figures as $A_{tip}$, $A_{bellows}$, and $A_{foot}$. As described below, the variation in spatial orientation of the central lumen axis A occurs both horizontally (reflected in FIG. 2B) and vertically (reflected in FIG. 3B) relative to an upright position of the interface device 20.

The tip 40 extends proximally from the bellows segment 42, and terminates at a tip end 46 opposite the bellows segment 42. As further shown in the view of FIGS. 3A and 3B, the tip end 46 is flared relative to a remainder of the tip 40. That is to say, in one embodiment the tip end 46 defines a proximally increasing outer diameter for more readily engaging or contacting a surface of the patient's naris upon insertion of the tip 40 within the naris. Further, and in one embodiment, a cross-sectional wall thickness of the tip end 46 is decreased as compared to a wall thickness of the remainder of the tip body 40 as best shown in FIG. 3B. That is to say, the tip 40 can be described as including the tip end 46 and a tip body 48, with the prong 22 being formed by a continuous side wall 50. With these definitions in mind, the side wall 50 tapers in thickness (proximally) along the tip end 46 to a thickness that is at least 25% less than a maximum nominal thickness of the side wall 50 along the tip body 48. This reduced wall thickness renders the tip end 46 highly compliant and thus less likely to create pressure points when pressed against an interior of the patient's naris.

A spatial orientation of the tip body 48 is dictated by an arrangement of the corresponding bellows segment 42/foot 44 as described below, with the prongs 22, 24 being arranged to each generally define an interior side 52a, 52b, respectively, and an exterior side 54a, 54b, respectively, as shown in FIG. 2A. The interior side 52a of the first prong 22 "faces" the interior side 52b of the second prong 24 (and vice-versa); the exterior side 54a or 54b is defined opposite the corresponding interior side 52a or 52b. With this in mind, the tip bodies 48 are, in one embodiment, configured in combination with spatial orientation dictated by the bellows segment 42/foot 44 such that the interior sides 52a, 52b along the tip bodies 48 are substantially parallel (e.g., with 5 degrees of a true parallel relationship), whereas the exterior sides 54a, 54b along the tip bodies 48 taper slightly toward one another in proximal extension. For example, a lateral distance between the interior sides 52a, 52b at the corresponding tip body 48/bellows segment 42 intersection is substantially the same as a lateral distance at the tip body 48/tip end 46 intersection; conversely, a lateral distance between the exterior sides 54a, 54b decreases from the corresponding tip body 48/bellows segment 42 intersection to the tip body 48/tip end 46 intersection. This one configuration of the tip bodies 48 establishes a first septal relief zone 56 (referenced generally in FIG. 2A) that limits possible formation of pressure points along the patient's septum (that is otherwise between the interior sides 52a, 52b of the tip bodies 48 upon insertion of the prongs 22, 24) due to the substantially parallel relationship. Instead, primary contact (preferably all contact) between the prongs 22, 24 and the patient's septum occurs only at the tip ends 46. For neonates having underdeveloped septums, this absence of pressure points essentially eliminates a recognized cause of septal necrosis found with use of conventional nasal prong devices. Conversely, the tapered relationship (relative to a true parallel relationship) established by the exterior sides 54a, 54b conforms to the expected naris anatomy (e.g., nasal orifice and nasal entrance). Alternatively, the tip bodies 48 can assume other shapes relative to the interior and/or exterior sides 52a, 52b, 54a, 54b.

Figure 3A:
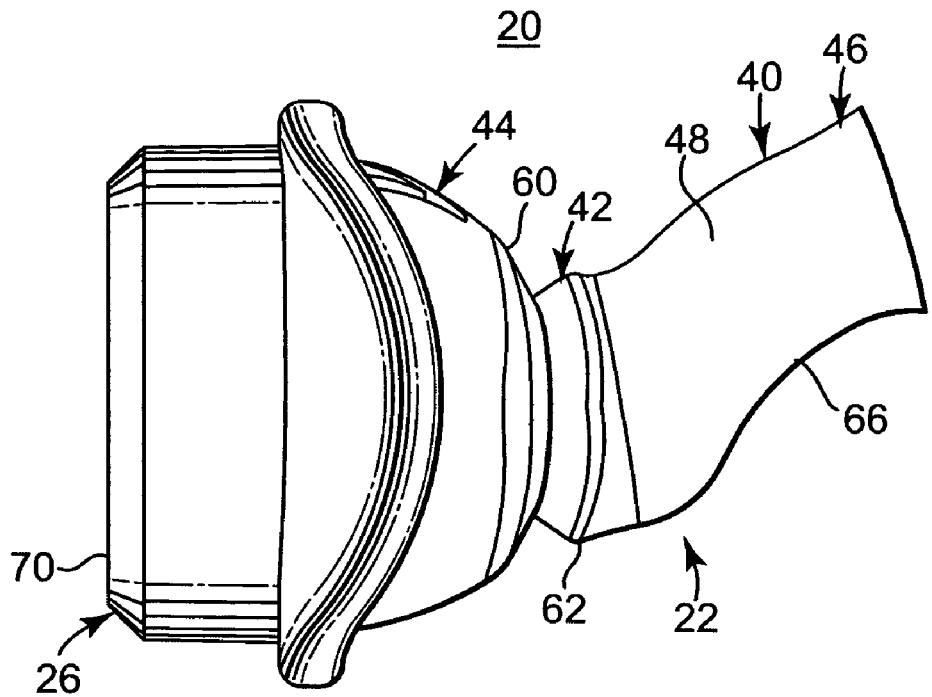
FIG. 3A is a side plan view of the interface device of FIG. 1.
Figure 3B:
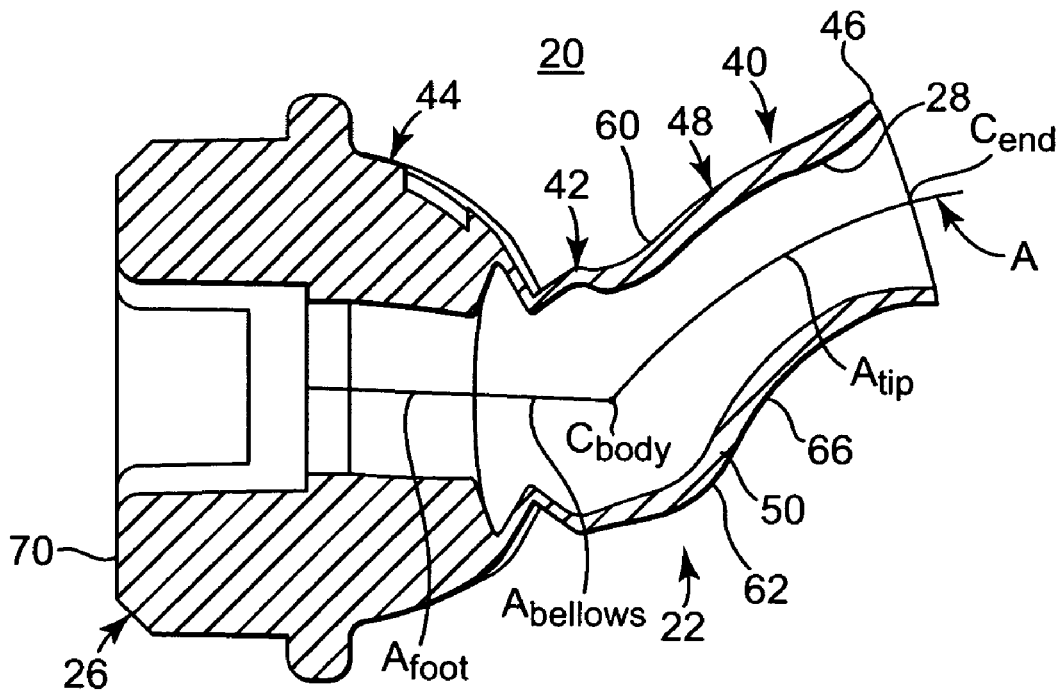
FIG. 3B is a side, longitudinal cross-sectional view of the interface device of FIG. 1.

An additional feature of the tip 40 in accordance with one embodiment is best reflected in the views of FIGS. 3A and 3B. To this end, FIGS. 3A and 3B depict the interface device 20 in an "upright" orientation whereby the prong 22 can be described as having or defining a top side 60 (referenced generally) and a bottom side 62 (referenced generally). Relative to the patient's anatomy, upon insertion into the naris, the top side 60 will reside closer to the patient's nasal bridge as compared to the bottom side 62; conversely, the bottom side 62 will reside more closely to the patient's upper lip as compared to the top side 60. With these conventions in mind, the tip body 48 defines a longitudinal curvature that approximates the expected naris anatomy, and further positions the base 26, and thus the nCPAP generator (not shown) otherwise attached to the base 26, at a desired position relative to the patient (i.e., off of the patient's face). For example, in one embodiment, a proximal region 66 of the tip body 48 has, in longitudinal (proximal) extension relative to the bellows segment 42, a convex curvature along the top side 60 and a concave curvature along the bottom side 62. In one embodiment, a radius of curvature associated with the proximal region top side 60 differs from that associated with the proximal region bottom side 62, with the proximal region top side 60 having a larger radius of curvature. Alternatively, the radius of curvature of the proximal region 66 can be uniform. Even further, in other embodiments, the tip body 48 exterior is linear in longitudinal extension. Along these same lines, in one embodiment, the central axis A of the lumen 28 as defined by the tip body 48 (i.e., $A_{tip}$) is arcuate or curved relative to a side plane (or vertical, longitudinal cross-section as shown in FIG. 3B) of the device 20; alternatively, the central axis $A_{tip}$ can be linear.

Regardless, longitudinal extension of the tip body 48 from the bellows segment 42 includes a transverse or radial component, such that the tip end 46 is transversely offset (e.g., vertically above) relative to the bellows segment 42 in the upright orientation of the interface device 20 as shown in FIGS. 3A and 3B. In one embodiment, this vertical offset is characterized by the central axis A of the lumen 28 along the bellows segment 42 (i.e., $A_{bellows}$) being transversely or vertically offset relative to the central axis A of the lumen 28 at the tip end 46 (in longitudinal, side planar view of the device 20). The vertical offset can alternatively be characterized relative to the tip body 48. More particularly, the tip end 46 defines a lumen center point $C_{end}$. Similarly, the tip body 48 defines a lumen center point $C_{body}$ at the intersection with the bellows segment 42 (i.e., a trailing end of the tip body 48). Relative to the upright orientation of FIG. 3B, the tip end center point $C_{end}$ is transversely above the tip body center point $C_{body}$. As a point of reference, as described below the bellows segment 42 is flexible, such that the tip 40 can pivot or deflect relative to the foot 44 with the bellows segment 42 internally flexing or deflecting. Thus, spatial relationships or attributes described herein are relative to the prong 22 in an undeflected or natural state.

The bellows segment 42 extends distally from the tip 40, and is configured to permit and facilitate pivoting and/or flexing of the tip 40 relative to the foot 44 (and relative to the base 26). The flexibility afforded by the bellows segment 42 can be accomplished with a variety of designs. For example, the bellows segment 42 is configured such that the tip 40 can pivot in a multitude of directions relative to the foot 44 and/or base 26 (e.g., vertically up or down, horizontally side-to-side, etc.), move distally toward the foot 44/base 26 (via collapsing of the bellows segment 42), etc. In one embodiment, however, the bellows segment 42 is configured to allow pivoting or swiveling of the tip 40 with minimal force and without kinking (i.e., the bellows segment 42 does not overtly collapse or fold over in a manner that would otherwise result in a substantial increase in flow resistance). To better understand this feature, a brief explanation of certain spatial features associated with the foot 44 and the base 26 is helpful.

As previously described, the base 26 facilitates assembly of the patient interface device 20 to an nCPAP generator (shown at 150 in FIG. 5A), and defines a distal or rear face 70. The rear face 70 abuts against a corresponding surface of the nCPAP generator, and thus defines a plane relative to which portions of the patient interface device 20 can be compared or described. In addition, the base 26 forms first and second passages 72, 74 that are fluidly connected to respective ones of the lumens 28, 30 as shown in FIG. 2B. In this regard, fluid connection between the lumens 28, 30 and the passages 72, 74, respectively, is achieved at an interface or transition of the respective foot 44 and the base 26.

With the above conventions in mind, and with specific reference to the longitudinal cross-sectional bottom view of FIG. 2B, in one embodiment, the bellows segment 42 is formed via the side wall 50 defining first, second, and third sections 90-94. The first section 90 extends proximally from the foot 44 to define a first bend angle W. The second section 92 extends proximally from the first section 90 to define a second bend angle X. The third section 94 extends proximally from the second section 92 to define a third bend angle Y. Finally, the third section 94 and the tip body 48 combine to define a fourth bend angle Z. In general terms and in one embodiment, the sections 90-94 combine to define a single outboard wall segment (at the intersection of the second and third sections 92, 94) and do not include or define an annular trough.

A transverse plane defined at an intersection of the first section 90 and the foot 44 is non-parallel relative to the plane of the rear face 70 as shown in FIG. 2B. That is to say, the interior side 80 at the first section 90/foot 44 intersection is longitudinally closer to the rear face 70 as compared to the exterior side 54a at the first section 90/foot 44 intersection. This characteristic is alternatively described by the interior side 52a of the foot 44 having a longitudinal length less than that of the exterior side 54a of the foot 44. Regardless, proximal extension of the first section 90 relative to the foot 44 imparts an inward "tilt" onto the bellows segment 42. Further, the first bend angle W varies about a circumference or perimeter of the first section 90. More particularly, the first bend angle W is greater at the exterior side 54a as compared to the interior side 52a, and is greater than 180° at least along the exterior side 54a such that as a whole, the first section 90 projects radially inwardly (relative to the central axis A of the lumen 28) in longitudinal (proximal) extension from the foot 44.

A spatial orientation of the second section 92 relative to the first section 90 continues the above-described inward "tilt", with the exterior side 82 at the second section 92/first section 90 intersection being longitudinally further from the rear face 70 as compared to the interior side 80 at the second section 92/first section 90 intersection. In one embodiment, the second bend angle X is substantially uniform about a circumference or perimeter of the first section 90/second section 92 intersection, but in alternative embodiments can vary. Regardless, the second bend angle X is less than 180°, preferably less than 120°, and even more preferably less than 90°, such that the second section 92 projects radially outwardly in longitudinal (proximal) extension from the first section 90. This, in turn, results in the lumen 28 having an increasing diameter relative to a longitudinal (proximal) extension of the second section 92 from the first section 90.

A spatial orientation and configuration of the third section 94 relative to the second section 92 compensates for the planar offset described above. In particular, the third bend angle Y, as defined by the proximal extension of the third section 94 from the second section 92, varies along a circumference or perimeter of the second section 92/third section 94 intersection, with the third bend angle Y being greater along the exterior side 82 as compared to the interior side 80. For example, in one embodiment, the third bend angle Y along the exterior side 54a approaches 270°, whereas the third bend angle Y along the interior side 52a is approximately 210°. Alternatively, other dimensional relationships are equally acceptable; preferably, however, an entirety of the third bend angle Y is greater than 180° such that the third section 94 projects radially inward with longitudinal (proximal) extension from the second section 92. In other words, the third section 94 defines the lumen 28 to have a proximally decreasing diameter. As a result of this spatial orientation, a longitudinal distance of the third section 94/tip body 48 interface relative to the rear face 70 is substantially uniform at the interior and exterior sides 52a, 54a.

Finally, the fourth bend angle Z as defined by the third section 94 and the tip body 48, varies about a circumference of the prong 22. More particularly, in one embodiment, the fourth bend angle Z is preferably greater along the interior side 52a as compared to the exterior side 54a. As a result, and relative to the bottom longitudinal view of FIG. 2B, the tip body 48 extends in a generally perpendicular fashion relative to a plane of the rear face 70.

The above-described bellows segment sections 90-94 and bend angles X-Z (and primarily, in one embodiment, the second and third section 92, 94 and the second bend angle X) combine to allow the bellows segment 42 to repeatedly pivot or swivel in virtually any direction as well as compress longitudinally, all without kinking. In addition, the bellows segments 42 collectively maintain the interior side 52a, 52b lateral spacing described above with respect to the tip bodies 48 so as to avoid overt contact with the patent's septum. With respect to the spatial orientation attribute, the first passage 72 formed by the base 26 defines a passage axis P. Relative to the passage axis P, the central axis of the foot 44 ($A_{foot}$) projects laterally outwardly with proximal extension of the foot 44 from the base 26. Conversely, the central axis of the bellows segment 42 ($A_{bellows}$) projects laterally inwardly with proximal extension of the bellows segment 42 from the foot 44. Finally, the central axis of the tip 44 ($A_{tip}$) projects primarily longitudinally (relative to a horizontal plane) with proximal extension of the tip 40 from the bellows segment 42. Thus, the tip 40 is laterally offset relative to bellows segment 42, with a majority of the bellows segment 42 surface area residing at the exterior side 54a (compared to the interior side 52a). Thus, the bellows segment 42 can be described as being non-symmetrical in one or more respects. For example, the bellows segment 42 is non-symmetrical relative to the central tip axis $A_{tip}$. Further, an exterior shape of the bellows segment 42 is non-symmetrical relative to the central bellows segment axis $A_{bellows}$.

Inward deflection or pivoting of the tip 44 is facilitated primarily by the second section 92 compressing toward the first section 90 along the interior side 52a, and expanding away from the first section 90 along the exterior side 54a (via the second bend angle X); a converse relationship occurs with outward deflection. The enhanced thickness and angular relationship of the second and third sections 92, 94 along the exterior side 54a ensures that this pivoting movement occurs without kinking and provides continuous support to the desired longitudinal extension of the tip 40. That is to say, by forming the bellows segment 42 to include laterally outwardly extending sections (as compared to a reduced thickness, longitudinal or annular trough), the bellows segment 42 provides a degree of lateral resistance to compression so that the tip 40 can be inserted through a nasal opening without collapsing. Conversely, while the bellows segment 42 along the interior side 52a also permits low force-induced pivoting, a structural mass is of a reduced size so as to maximize the lateral distance between the interior sides 52a, 52b. Thus, a second septal relief zone 100 (referenced generally in FIG. 2A) is established between the bellows segments 42 as a continuation of the first septal relief zone 56 (established between the tip bodies 48).

Figure 2C:
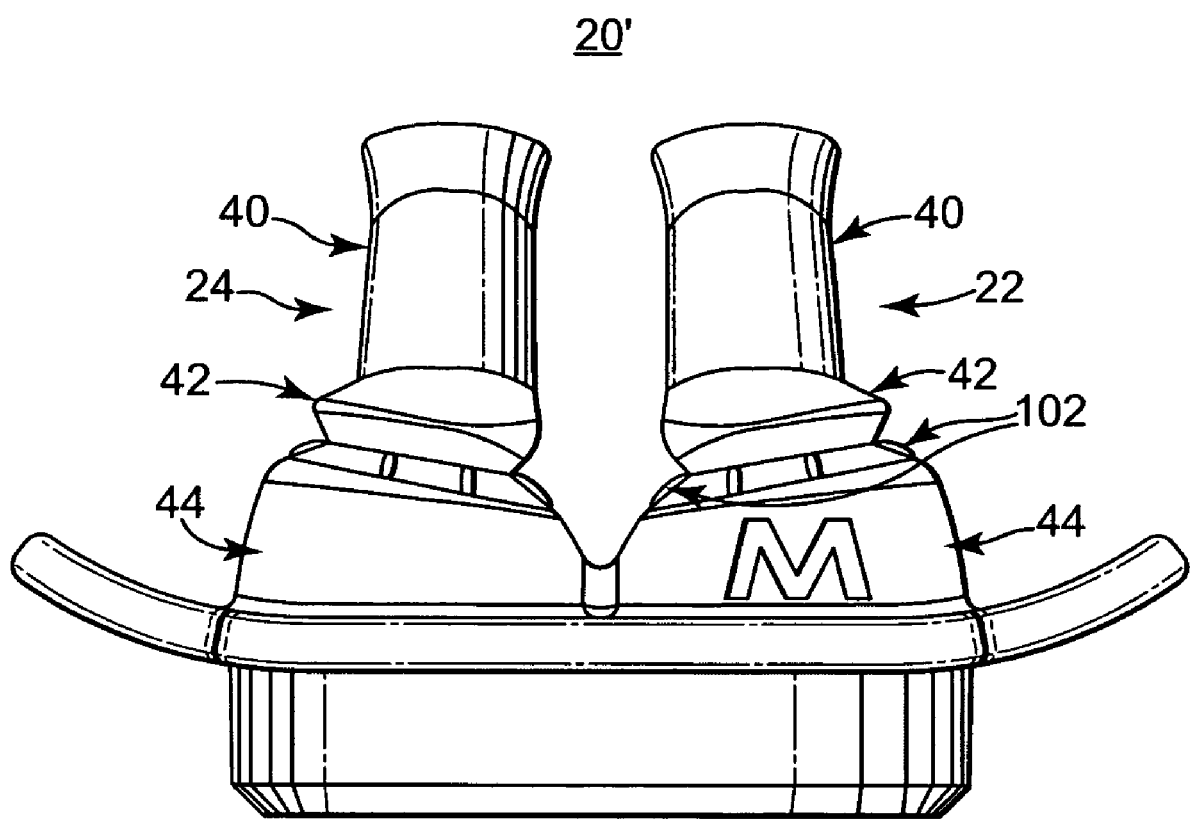
FIG. 2C is a bottom plan view of an alternative embodiment infant nasal interface prong device.

The above-described configuration of the bellows segment 42 results in the prong 22 being able to accommodate for unexpected anatomical configurations of, or deviations in, the patient's septum during use. When the tip 40 inserted within the patient's naris, the bellows segment 42 essentially causes the tip 40, and in particular the tip end 46, to search for the septum or interior region of the naris via the inward angular orientation, and maintains a seal against the septum. In alternative embodiments, however, the bellows segment 42 can assume a variety of other configurations. For example, the bellows segment 42 can have or define more or less than three of the sections 90-94, and the bend angles W-Z can differ from that previously described. Further, the sections 90-94 and/or the bend angles W-Z can be selected to create a directional bias within the bellows segment 42 whereby the bellows segment 42 more readily deflects in one direction as compared to another. In other embodiments, and as shown for example by the alternative embodiment infant nasal interface prong device 20' of FIG. 2C, one or more ribs 102 can be formed adjacent or along the bellows segment 42. The ribs 102 provide a tactile indication when the bellows segment 42 is overtly compressed or collapsed, otherwise implicating naris insertion complications (e.g., the ribs 102 resist further contraction when contacted, and can "force" the bellow segment 42 to revert back toward an uncompressed state). The ribs 102 can assume a variety of forms, and can be provided at various locations along one or both of the foot 44 and/or the bellows segment 42.

Returning to the device 20 of FIG. 1, to further enhance a flexibility of the bellows segment 42, in one embodiment at least a portion of the bellows segment 42 is characterized by a reduced thickness of the side wall 50 as compared to a thickness of the side wall 50 along the tip body 48 and the base 26. For example, and as shown in FIG. 3B, in one embodiment an entirety of the bellows segment 42, including the first, second, and third sections 90-94, are each characterized by a wall thickness that is much less than that of the base 26. Further, at least portions of the first, second, and third sections 90-94 have a wall thickness less than that of the tip body 48. For example, in one embodiment, at least a portion of the bellows segment 42 (e.g., the first and second segment 90, 92 in regions of one or both of the interior and exterior sides 52a, 54a) has a wall thickness that is at least 25% less than a maximum nominal wall thickness of the tip body 48. Regardless, by forming at least a portion of the bellows segment 42 to have a reduced wall thickness as compared to the base 26 and the tip body 48, an overall flexibility of the bellows segment 42 is enhanced, yet the base 26 and the tip body 48 are provided with sufficient structural strength and rigidity to maintain the prong 22 (or 24) in a desired shape and orientation during naris insertion and delivery of CPAP therapy.

As previously described, the foot 44 extends from the base 26 and positions the bellows segment 42 (and thus the tip body 48) at a desired angular orientation relative to the rear face 70 of the base 26. In addition, and in one embodiment, the foot 44 of the first prong 22 combines with the foot 44 of the second prong 24 to continue the second septal relief zone (designated at 100 in FIG. 2A) described above. More particularly, relative to the bottom planar view, the interior side 52a at the foot 44 includes a radial outward component in proximal extension from the base 26. This, in turn, establishes a transverse spacing between the respective feet 44, resulting in a third septal relief zone 104 (referenced generally in FIG. 2A). The third septal relief zone 104 minimizes overt contact with the patient's nasal septal area (as well as the exterior skin thereof) upon insertion of the prongs 22, 24 within the patient's nares, thus minimizing skin breakdown in this delicate area and increasing patient comfort. In one embodiment, the septal relief zones 56, 100, 104 are collectively configured such that a minimum lateral distance between the prongs 22, 24 is established at the tip ends 46. Alternatively, the foot 44 can assume a variety of other configurations, in fact, in some alternative embodiments, the foot 44 is eliminated.

Figure 4:
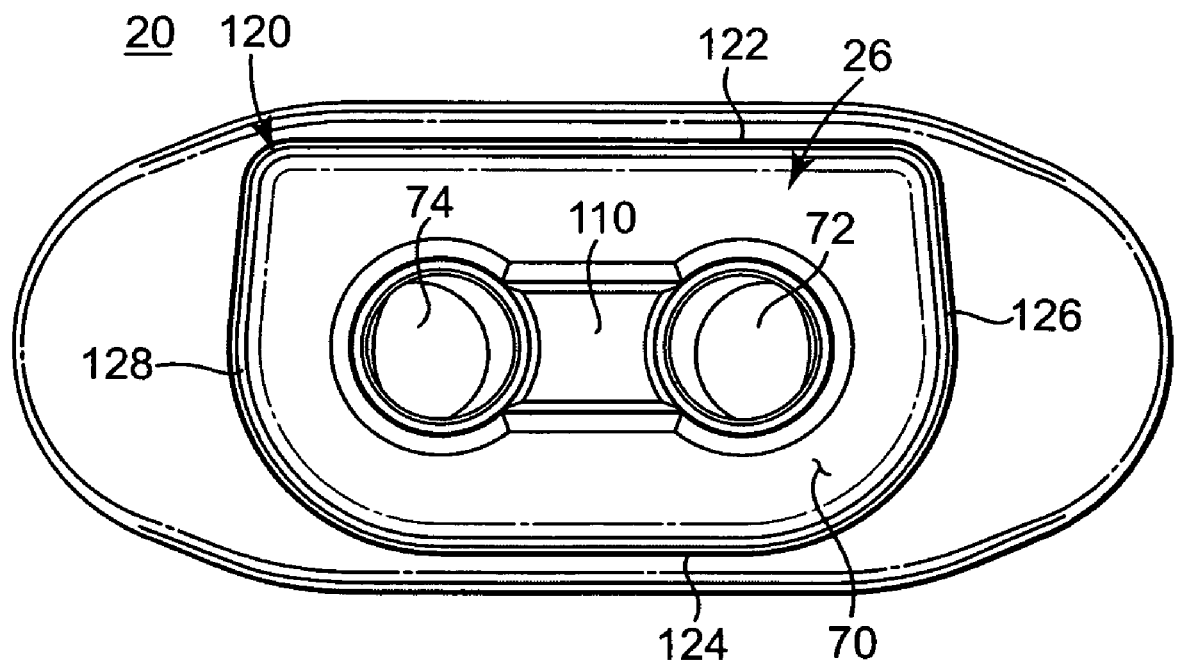
FIG. 4 is a rear view of the interface device of FIG. 1.

With reference to FIGS. 2B and 4, the base 26 extends from the feet 44 and, as previously described, forms the first and second passages 72, 74, as well as a channel 110. Once again, the passages 72, 74 extend in a longitudinal fashion through a thickness of the base 26, and are fluidly connected to respective ones of the lumens 28, 30. As described in greater detail below, the passages 72, 74 are sized for assembly over corresponding components of a CPAP generator device (shown at 150 in FIG. 5C), and thus are open relative to the rear face 70 of the base 26. Thus, the passages 72, 74 provide mechanisms for fluidly connecting the CPAP generator device to the lumens 28, 30. The channel 110 extends between, and is fluidly connected to, the passages 72, 74. In addition, while the channel 110 is open at the rear face 70, the channel 110 is not directly fluidly connected to the lumens 28, 30. As described in greater detail below, the channel 110 is sized and shaped in accordance with certain features of one embodiment CPAP generator, and facilitates sampling or tapping of pressure within the device. Thus, the channel 110 can assume a wide variety of forms in terms of size, shape, etc. In fact, in alternative embodiments, the channel 110 is eliminated.

The base 26 is, in one embodiment, sized and shaped for interfacing with a corresponding component of a CPAP generator (shown at 150 in FIG. 5C) and fluidly connecting the passages 72, 74 to the CPAP generator device. In this regard, an exterior of the base 26 defines a perimeter 120 (best shown in FIG. 4) that includes opposing first and second side edges 122, 124, and opposing first and second end edges 126, 128. In one embodiment, a perimeter shape of an intersection or transition of the first side edge 122 to each of the end edges 126, 128 differs from the perimeter shape of the transition or intersection of the second side edge 124 with the end edges 126, 128. For example, in one embodiment, a transition of the second side edge 124 to each of the end edges 126, 128 is characterized as being arcuate or curved in perimeter shape, having a relatively large radius of curvature. In contrast, a transition of the first side edge 122 to each of the end edges 126, 128 is characterized as defining a relatively distinct corner, having a radius of curvature that is less than that of the second side edge 124/end edge 126, 128 transitions. Thus, a lateral length of the first side edge 122 is greater than that of the second side edge 124. This one preferred configuration of the perimeter 120 corresponds with the feature(s) of the CPAP generator device (described below) so as to ensure a desired, proper orientation of the base 26, and thus of the prongs 22, 24, relative to the CPAP generator device upon final assembly.

Figure 5A:
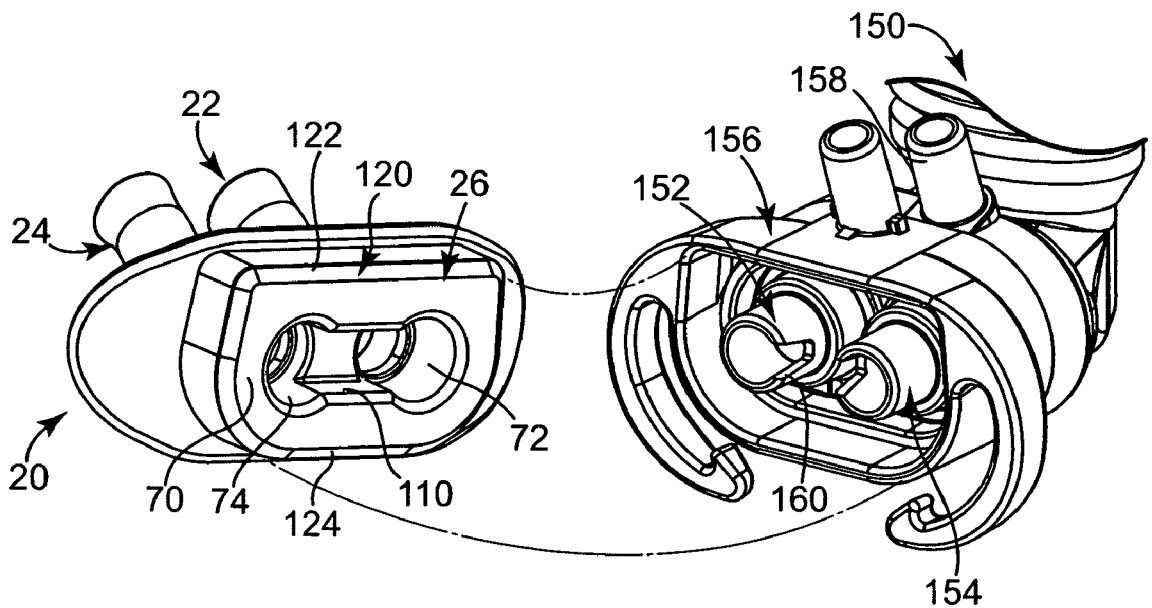
FIG. 5A is an exploded, perspective view of an nCPAP device in accordance with principles of the present invention including the interface device of FIG. 1 and an nCPAP generator.

For example, FIG. 5A illustrates a portion of one embodiment CPAP generator device 150 with which the patient interface device 20 is useful in accordance with principles of the present invention. Details on the generator device 150 are provided in U.S. application Ser. No. _____ entitled "Nasal Continuous Positive Airway Pressure Device and System," filed on even date herewith and having attorney docket number RT-6274, the teachings of which are incorporated herein by reference. In general terms, the CPAP generator device 150 includes first and second tubes 152, 154 laterally surrounded by a housing 156 and fluidly connected to a fluid supply port 158. During use, the CPAP generator device 150 receives fluid flow via the support port 158 and generates a continuous positive airway pressure within each of the tubes 152, 154. With these general concepts in mind, the passages 72, 74 of the base 26 are sized for mating over a respective one of the tubes 152, 154, and the base 26 is sized for being received and frictionally retained within the housing 156. In this regard, an interior perimeter shape of the housing 156 corresponds with the perimeter 120 of the base 26 as previously described.

In particular, the differing lengths of the side edges 122, 124, as well as the curved and corner-shaped transition regions previously described prevents a user from accidentally attempting to insert the base 26 into the housing 156 in an orientation opposite to that desired (i.e., the upright orientation). That is to say, the base 26/housing 156 interface permits only one orientation of the base 26, and thus of the prongs 22, 24, relative to the CPAP generator device 150.

Figure 5B:
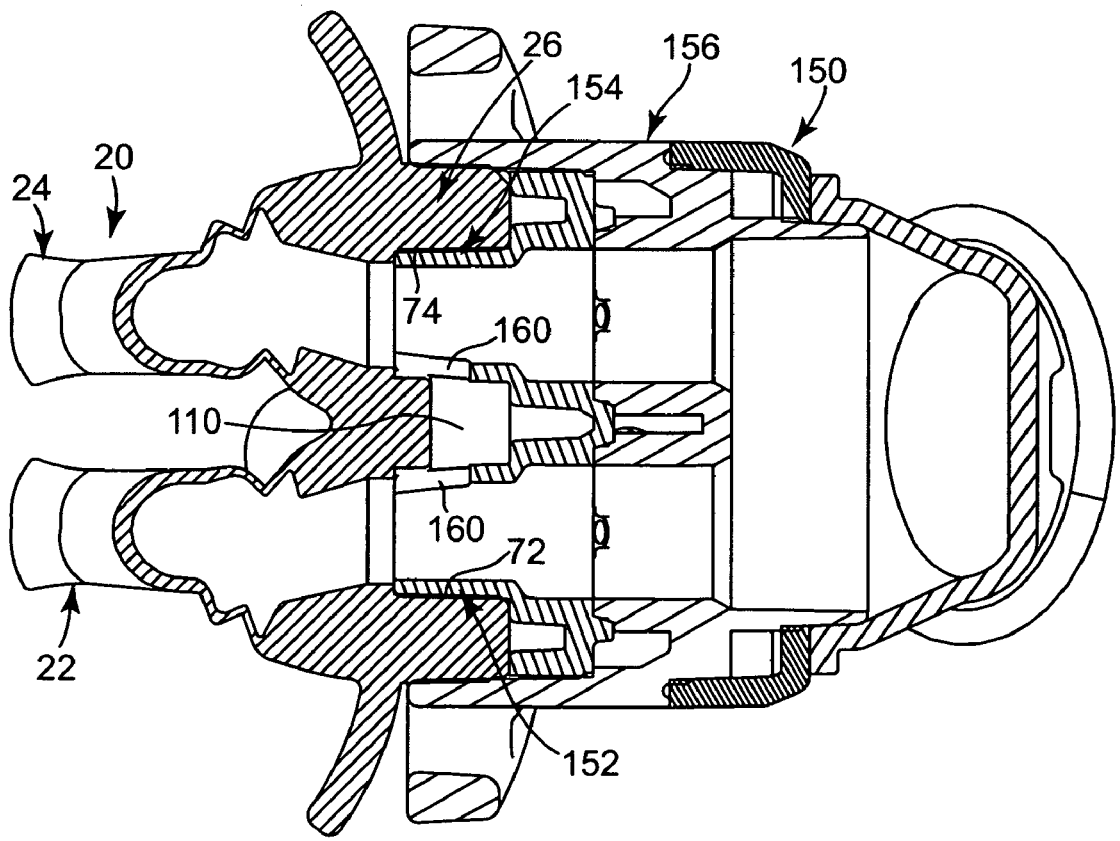
FIG. 5B is a cross-sectional view of the nCPAP device of FIG. 5A upon final assembly.

FIG. 5B partially illustrates assembly of the base 26 to the CPAP generator device 150, and in particular, the first passage 72 over the first tube 152 and the second passage 74 over the second tube 154. As shown, each of the tubes 152, 154 includes a radial slot 160 that is otherwise fluidly connected to the channel 110 upon final assembly of the base 26 within the housing 156. With this one arrangement, then, airflow within the tubes 152, 154 is allowed to flow from the tubes 152, 154/base 26 interface via the channel 110, for subsequent pressure monitoring. In one embodiment, a depth and a width of the channel 110 is correlated with a diameter of the passages 72, 74 to minimize formation of back pressure within the device 20 while still affording the ability to accurately sample pressure being delivered to the patient. To this end, it has surprisingly been found that by forming the channel 110 to have a depth that is at least 30% of the diameter of either passage 72, 74 (at the rear face 70) and a width that is at least 25% of either the passage 72, 74 diameters, significant back pressure will not be generated at expected CPAP levels.

Although the patient interface device 20 has been described in connection with certain features of the CPAP generator device 150, a wide variety of differing CPAP device configurations can also be employed. That is to say, the patient interface device 20 in accordance with principles of the present invention is not limited to any one particular CPAP device design.

The infant nasal interface prong device in accordance with principles of the present invention provides a marked improvement over previous prong designs. The thin-walled, bellows segment allows the prong to easily pivot and/or flex relative to the base (and thus the CPAP generator to which the base is assembled). This attribute allows the patient interface device to accommodate any misalignments of the CPAP generator and/or related fixation devices relative to the patient, and further minimizes or eliminates pressure point(s) on the infant's/patient's nasal or facial anatomy that might otherwise be created by CPAP generator misalignment. To this end, the curved shape of the prongs more closely matches an expected anatomy of the patient's naris, and allows the CPAP generator device to be located "off" of the patient's face. Finally, the inward bias of the prongs readily accommodates deviations in the patient's septal anatomy.

Although the present invention has been described with reference to preferred embodiments, workers skilled in the art will recognize that changes can be made in form and detail without departing from the spirit and scope of the present invention.

What is claimed is:

1. An infant nasal interface prong device for use with a continuous positive airway pressure (CPAP) system, the device comprising:
   first and second nasal prongs each including:
      a bellows segment,
      a tip extending from the bellows segment, the tip adapted for insertion within an infant's naris and terminating in a tip end opposite the bellows segment, the tip further including a tip body extending distal the tip end and wherein relative to an orientation upon insertion within the infant's naris, the tip body defines a top side and a bottom side, wherein at least a portion of the top side forms a convex curve and at least a portion of the bottom side forms a concave curve;
      a lumen extending through the prong and open at the tip end,
      wherein in an undeflected state, a central axis of the lumen as defined by the bellows segment is transversely offset from a central axis of the lumen as defined by the tip end; and
   a base connected to each of the nasal prongs and adapted for coupling to a CPAP generator, the base forming first and second passages fluidly connected to respective ones of the first and second lumens.

2. The infant nasal interface device of claim 1, wherein relative to an upright orientation of the device, each prong is characterized by the central axis of the lumen as defined by the bellows segment being vertically offset from the central axis of the lumen as defined by the tip end in an undeflected state.

3. The infant nasal interface device of claim 1, wherein a central axis of the first passage is transversely offset from the central axis of the first lumen defined by the corresponding tip end.

4. The infant nasal interface device of claim 1, wherein the central axis of each prong is non-linear.

5. The infant nasal interface device of claim 1, wherein relative to an upright of the device, each prong is characterized by the central axis of the lumen as defined by the bellows segment being horizontally offset from the central axis of the lumen as defined by the tip in an undeflected state.

6. The infant nasal interface device of claim 1, wherein each of the prongs defines an interior side relative to the opposing prong, and further wherein in the undeflected state, the interior sides are substantially parallel.

7. The infant nasal interface device of claim 1, wherein the bellows segment is non-symmetrical with respect to the corresponding central axis.

8. The infant nasal interface device of claim 1, wherein the bellows segment includes a plurality of sections combining to define a plurality of bends each having a bend angle, and further wherein the bellows segment is configured such that in an undeflected state, at least one of the bend angles is non-uniform about a circumference of the corresponding prong.

9. The infant nasal interface device of claim 8, wherein the prongs extend in a juxtaposed fashion relative to the base such that each prong defines an interior side and exterior side, and further wherein in an undeflected state, at least one of the bend angles differs at the interior side as compared to the exterior side.

10. The infant nasal interface device of claim 1, wherein the bellows segment includes a trailing end opposite the tip end, and further wherein in an undeflected state, a transverse plane defined by the trailing end is not perpendicular to the central axis of the lumen at the tip end.

11. The infant nasal interface device of claim 1, wherein each prong is formed by a continuous wall having a nominal thickness along the tip that is greater than a thickness of the wall along at least a portion of the bellows segment.

12. The infant nasal interface device of claim 1, wherein each prong further includes a foot extending from the corresponding bellows segment to the base, and further wherein a nominal wall thickness of the foot is greater than a wall thickness along at least a portion of the corresponding bellows segment.

13. The infant nasal interface device of claim 12, wherein the feet are configured to collectively define a septal relief zone.

14. The infant nasal interface device of claim 12, wherein each prong is configured such that in an undeflected state, the central axis of the lumen along the foot is not parallel with the central axis of the lumen at the tip end.

15. The infant nasal interface device of claim 12, wherein the tip of each prong includes a tip body extending distally from the tip end, and further wherein in an undeflected state, the central axis of the lumen along the foot is not parallel with the central axis of the lumen along the tip body.

16. The infant nasal interface device of claim 1, wherein the base is configured to define, in transverse cross-section, opposed first and second side edges and opposed first and second end edges, and further wherein a transition between a first end edge and the first side edge defines a curve and a transition between the first end edge and the second side edge is a corner.

17. The infant nasal interface device of claim 1, wherein the base further forms a channel extending between, and fluidly connected to, the first and second passages.

18. The infant nasal interface device of claim 17, wherein the base defines a rear face, the prongs extending from the base opposite the rear face, and further wherein the channel is open at the rear face and has a depth less than a length of the passages.

19. The infant nasal interface device of claim 1, wherein for each of the prongs, relative to a cross-section taken along a plane commonly defined by the central axes of the first and second passages, the central axis of the lumen as defined by the bellows segment is transversely offset from the central axis of the lumen as defined at the tip end when the prong is in an undeflected state.

20. An infant nasal continuous positive airway pressure (nCPAP) device for use in an nCPAP system, the device comprising:
  an nCPAP generator including a housing laterally surrounding first and second tubes, the nCPAP generator adapted to generate a continuous positive airway pressure within each of the tubes; and
  an infant nasal interface prong device mounted to the tubes, the infant nasal interface prong device comprising:
    first and second nasal prongs each including:
      a bellows segment,
      a tip extending from a bellows segment, the tip adapted for insertion within an infant's naris and terminating in a tip end opposite the bellows segment, wherein the tip includes a tip body extending distal the tip end, and further wherein relative to an orientation upon insertion within an infant's naris, the tip body defines a top side and a bottom side, and further wherein at least a portion of the top side forms a convex curve and at least a portion of the bottom side forms a concave curve,
      a lumen extending through the prong and open at the distal end,
      wherein in an undeflected state, a central axis of the lumen as defined by the bellows segment is transversely offset from a central axis of the lumen defined by the tip end, and
    a base sized to be received by the housing, the base being connected to each of the nasal prongs and forming first and second passages fluidly connected to respective ones of the first and second lumens, wherein the passages are fluidly connected to respective ones of the first and second tubes upon final assembly;
  wherein the base and the housing define corresponding, non-symmetrical perimeter shapes.

21. The nCPAP device of claim 20, wherein the device is configured such that insertion of the base into the housing simultaneously fluidly connects the passages with the tubes, respectively.

22. An infant nasal interface prong device for use with a continuous positive airway pressure (CPAP) system, the device comprising:
  first and second nasal prongs each including:
    a bellows segment,
    a tip including a tip body extending from the bellows segment and terminating at a tip end, the tip adapted for insertion within an infant's naris, wherein the tip body defines a top side forming a convex curve and a bottom side forming a concave curve,
    a lumen extending through the prong and open at the tip end,
    wherein in an undeflected state, a central axis of the lumen defined by the bellows segment is transversely offset from a central axis of the lumen defined by the tip end; and
  a base connected to each of the nasal prongs and adapted for coupling to a CPAP generator, the base forming first and second passages fluidly connected to respective ones of the first and second lumens;
  wherein the first and second prongs extend in a juxtaposed fashion relative to the base, with the bellows segment of each of the prongs being non-symmetrical relative to an axis of the tip body.

23. An infant nasal interface prong device for use with a continuous positive airway pressure (CPAP) system, the device comprising:
  first and second nasal prongs each including:
    a bellows segment,
    a tip extending from the bellows segment, the tip adapted for insertion within an infant's naris and terminating in a tip end opposite the bellows segment,
    a lumen extending through the prong and open at the tip end,
    wherein in an undeflected state, a central axis of the lumen as defined by the bellows segment is transversely offset from a central axis of the lumen as defined by the tip end;
  a base connected to each of the nasal prongs and adapted for coupling to a CPAP generator, the base forming first and second passages fluidly connected to respective ones of the first and second lumens; and
  wherein each of the prongs defines an interior side relative to the opposing prong, and further wherein in the undeflected state, the interior sides are substantially parallel.

24. An infant nasal interface prong device for use with a continuous positive airway pressure (CPAP) system, the device comprising:
  first and second nasal prongs each including:
    a bellows segment, a tip extending from the bellows segment, the tip adapted for insertion within an infant's naris and terminating in a tip end opposite the bellows segment, a lumen extending through the prong and open at the tip end, wherein in an undeflected state, a central axis of the lumen as defined by the bellows segment is transversely offset from a central axis of the lumen as defined by the tip end, further wherein the bellows segment includes a trailing end opposite the tip end, and further wherein in the undeflected state, a transverse plane defined by the trailing end is not perpendicular to the central axis of the lumen at the tip end; and a base connected to each of the nasal prongs and adapted for coupling to a CPAP generator, the base forming first and second passages fluidly connected to respective ones of the first and second lumens.

25. An infant nasal interface prong device for use with a continuous positive airway pressure (CPAP) system, the device comprising:

first and second nasal prongs each including:

a bellows segment, a tip extending from the bellows segment, the tip adapted for insertion within an infant's naris and terminating in a tip end opposite the bellows segment, a lumen extending through the prong and open at the tip end, wherein in an undeflected state, a central axis of the lumen as defined by the bellows segment is transversely offset from a central axis of the lumen as defined by the tip end;

a base connected to each of the nasal prongs and adapted for coupling to a CPAP generator, the base forming first and second passages fluidly connected to respective ones of the first and second lumens; and wherein each bellows segment includes a foot extending from the corresponding bellows segment to the base, and further wherein a nominal wall thickness of the foot is greater than a wall thickness along at least a portion of the corresponding bellows segment.

26. The infant nasal interface device of claim 25, wherein the feet are configured to collectively define a septal relief zone.

27. The infant nasal interface device of claim 25, wherein each prong is configured such that in an undeflected state, the central axis of the lumen along the foot is not parallel with the central axis of the lumen at the tip end.

28. The infant nasal interface device of claim 25, wherein the tip of each prong includes a tip body extending distally from the tip end, and further wherein in an undeflected state, the central axis of the lumen along the foot is not parallel with the central axis of the lumen along the tip body.

* * * * *

UNITED STATES PATENT AND TRADEMARK OFFICE
CERTIFICATE OF CORRECTION

PATENT NO. : 7,640,934 B2 Page 1 of 1
APPLICATION NO. : 11/292808
DATED : January 5, 2010
INVENTOR(S) : Chris Zollinger et al.

It is certified that error appears in the above-identified patent and that said Letters Patent is hereby corrected as shown below:

Column 4, line 24, please delete "effectively"floats"" and insert --effectively "floats"-- therefor.

Column 4, line 29, please delete "as"proximal"" and insert --as "proximal"-- therefor.

Column 4, line 29, please delete "and"distal"" and insert --and "distal"-- therefor.

Column 4, line 33, please delete "compared"distal"." and insert --compared "distal".-- therefor.

Column 5, line 55, please delete "by." and insert --by-- therefor.

Column 8, line 27, please delete "side52a," and insert --side 52a,-- therefor.

Column 12, line 31, in Claim 2, please delete "undefiected" and insert --undeflected-- therefor.

Column 12, line 43, in Claim 5, please delete "undefiected" and insert --undeflected-- therefor.

Column 12, line 46, in Claim 6, please delete "undefiected" and insert --undeflected-- therefor.

Column 12, line 55, in Claim 8, please delete "undefiected" and insert --undeflected-- therefor.

Column 12, line 60, in Claim 9, please delete "undefiected" and insert --undeflected-- therefor.

Column 13, line 15, in Claim 14, please delete "undefiected" and insert --undeflected-- therefor.

Column 13, line 60, in Claim 20, please delete "end." and insert --end,-- therefor.

Column 13, line 61, in Claim 20, please delete "naris." and insert --naris,-- therefor.

Column 13, line 67, in Claim 20, please delete "distal" and insert --tip-- therefor.

Column 14, line 61-62, in Claim 23, please delete "undefiected" and insert --undeflected-- therefor.

Column 15, line 6, in Claim 24, please delete "undefiected" and insert --undeflected-- therefor.

Signed and Sealed this

Sixteenth Day of March, 2010

David J. Kappos
*Director of the United States Patent and Trademark Office*